United States Patent [19]

Allen et al.

[11] Patent Number: 5,155,025
[45] Date of Patent: Oct. 13, 1992

[54] HYDROGEN PEROXIDE STABILIZATION IN ASSAYS

[75] Inventors: Michael P. Allen, Sunnyvale; Sheng-Fen Li, Milpitas, both of Calif.

[73] Assignee: ChemTrak, Sunnyvale, Calif.

[21] Appl. No.: 837,579

[22] Filed: Feb. 18, 1992

Related U.S. Application Data

[63] Continuation of Ser. No. 325,448, Mar. 17, 1989, abandoned.

[51] Int. Cl.$^5$ ............ C12Q 1/60; C12Q 1/28
[52] U.S. Cl. .................... 435/11; 435/14; 435/25; 435/262; 435/805; 435/28; 436/11; 436/13; 436/14; 436/16; 436/63; 436/167; 436/169
[58] Field of Search .......... 435/11, 14, 25, 262, 435/805, 28; 436/11, 13, 14, 16, 63, 167, 169

[56] References Cited

U.S. PATENT DOCUMENTS

| | | | |
|---|---|---|---|
| 3,293,146 | 12/1966 | Free et al. | 435/18 |
| 3,298,789 | 1/1967 | Mast | 435/25 |
| 3,362,886 | 1/1968 | Rupe | 435/14 |
| 3,975,161 | 8/1976 | Svoboda et al. | 436/63 |

OTHER PUBLICATIONS

Dialog Abstract of U.S. Pat. No. 3,687,627, Neil, 1972.
Dialog Abstract of U.S. Pat. No. 3,681,022, Kibbel et al, 1972.
Chemical Abstract, Li et al., No. 108(9)71600e, J. Histochem. Cytochem., 1987.
Chemical Abstract No. 111(3)20528s, Kataoka et al., Patent No. JP-88108263, 1988.
Derwent Abstract Accession No. 81-77439D/42, Patent No. SU798590, Solntseva et al, 1981.

*Primary Examiner*—Amelia Burgess Yarbrough
*Attorney, Agent, or Firm*—Bertram I. Rowland

[57] ABSTRACT

Hydrogen peroxide stabilized in the presence of blood components by the addition of a metal oxide oxidant, an anionic chelating agent, particularly hydroxylic carboxylate and nitroprusside, and a catalase inhibitor. The composition finds particular application for stabilizing hydrogen peroxide in a diagnostic assay on a bibulous support.

20 Claims, No Drawings

HYDROGEN PEROXIDE STABILIZATION IN ASSAYS

This is a continuation of application Ser. No. 07/325,448, filed Mar. 17, 1989, now abandoned.

TECHNICAL FIELD

The technical field of the subject invention concerns diagnostic assays or other systems requiring stabilization of hydrogen peroxide.

BACKGROUND

In many assays, hydrogen peroxide is employed as a reagent. When the assays are quantitative or semi-quantitative, it is necessary that the hydrogen peroxide react in the manner intended to produce a detectable signal, usually chromogen formation. In many assays, blood, or blood derivatives such as serum or plasma are present, where the blood sample contains a complex mixture of components. These components vary from individual to individual and, it is found can have an effect on the quantitation of hydrogen peroxide. It is therefore important to provide systems which prevent the reaction of hydrogen peroxide by pathways other than the desired assay pathway.

RELEVANT LITERATURE

Co-pending Application Ser. No. 064,883, filed Jun. 22, 1987, describes a solid phase diagnostic assay employing hydrogen peroxide as a reagent.

And, co-pending Application Ser. No. 195,881, filed May 19, 1988 which describes a solid phase diagnostic assay where serum components are enzymatically converted to hydrogen peroxide which is subsequently used to generate a detectable signal.

SUMMARY OF THE INVENTION

Hydrogen peroxide is stabilized in the presence of blood or red blood cell free blood by combining a mixture of a chelating agent, a metal oxide oxidant, nitroprusside and preferably a catalase inhibitor. These compositions are combined in amounts sufficient to prevent reaction of hydrogen peroxide with components of the blood during the course of the assay determination.

DESCRIPTION OF THE SPECIFIC EMBODIMENTS

In systems employing blood, or red blood cell free blood, e.g. plasma or serum, where hydrogen peroxide is employed as a reagent to quantitate a component in the blood sample, a formulation is provided for stabilizing the hydrogen peroxide to prevent its reaction by pathways other than the assay pathway. Particularly, the formulation comprises a chelating agent, particularly a hydroxylated carboxylate, a metal oxide oxidant, particularly stannate, nitroprusside, and a catalase inhibitor, particularly sodium azide.

The additives are combined, so that the chelating agent, metal oxide and nitroprusside have a molar ratio of about 0.2-5:0.2-5:0.2-5, preferably about 0.5-2:0.5-2:0.5-2. Desirably, the various additives are equimolar. The sodium azide will be present primarily as a catalase inhibitor but also as a preservative, and is generally present in minor amount, when present, generally from about $1 \times 10^{-4}$ to 0.1 weight percent of the wet or dry formulation.

The formulation may take many forms. The formulation may be added to the assay medium during the assay. Alternatively, the formulation may be absorbed by a solid substrate, so that it dissolves into the assay medium upon addition of the assay medium to the substrate. The concentration of the various essential components in the assay medium will generally range from about 0.0001 to 0.5, more usually from about 0.001 to 0.1M. When impregnating a bibulous substrate, the solution employed to impregnate the bibulous substrate will generally range from about 0.005 to 0.1, more usually from about 0.01 to 0.05M for each of the components. The azide will generally range from about 0.005 to 0.1%. The compositions will usually be buffered at a pH of about 6 to 8, usually about 7 with a conventional buffer, e.g. phosphate at a concentration generally in the range of about 0.05 to 0.75M.

The subject compositions find particular use with diagnostic assays which employ an oxidase as a reagent, where the reaction of the oxidase is to produce hydrogen peroxide. Various enzymes may be employed, such as glucose oxidase, cholesterol oxidase, uric oxidase, alcohol oxidase, xanthine oxidase and the like. These enzymes will be used in conventional ways and in conventional amounts, in accordance with the particular assay involved.

Where the stabilizing formulation is applied to a bibulous support, various supports may be employed, such as cellulosic supports, e.g. paper, cellulose acetate, cellulose nitrate, glass fibers, or the like. Particularly, the bibulous support may serve as a reagent pad, where other reagents are also bound to the pad, particularly the enzyme reagent which results in formation of hydrogen peroxide.

Exemplary of the subject invention is the use of a reagent pad, where plasma is added to the pad for initiation of the assay. To the reagent pad is bound the oxidase, for example, for a glucose assay, glucose oxidase, for a cholesterol assay, cholesterol esterase and cholesterol oxidase, and a mixture of detergents, the subject formulation, and a mixture of enzyme stabilizers. Particularly, the detergents will be about a total of 0.10 to 10 weight percent of the solution applied to the pad and will be a mixture of non-ionic and anionic detergents. The enzyme stabilizers may include various additives, such as sugars in from about 0.1 to 20 dry weight percent, proteins, gum arabic, non-ionic detergents, where the total amount of the enzyme stabilizers will generally range from about 0.5 to 10, more usually from about 1 to 5 weight percent of the solution. The amount of enzyme will vary, depending upon the assay, and will generally be present in an amount of from about 1 to 500 units per ml.

In the case of the cholesterol assay as illustrative of other assays, the impregnating solution will have from about 2 to 100 units/ml of the two enzymes, cholesterol esterase and cholesterol oxidase. The detergents will be in total weight from about 0.1 to 5 weight percent of the medium, while in the case of mixtures the weight of the non-ionic detergents may be from about 10 to 90%, usually from about 25 to 75 weight percent of the total detergent mixture. The binding agents will generally be in the range of about 0.2 to 10, more usually from about 1 to 5 weight percent of the medium. A preservative or hydrogen bonding agent may be present in from about 1 to 20 weight percent, more usually from about 2 to 10 weight percent. The remaining additives will generally be present in total amount in less than about 10 weight percent, more usually in less than about 5 weight percent. The remaining composition may be water, nonreactive ingredients, excipients, extenders, and the like.

After allowing the reagent pad to absorb the solution, the solution may be dried and may then be used as appropriate. In carrying out the assay, the plasma is applied to the reagent pad, so as to be absorbed by the reagent pad, whereby hydrogen peroxide is produced. Any technique may then be used for determining the hydrogen peroxide, usually employing horseradish peroxidase and a chromogen, where the chromogen may produce a detectable signal, usually light absorption.

An assay may be carried out by impregnating a sample pad which serves as a bridge between two bibulous members. A first bibulous member serves to receive the transport solution, which may or may not have reaction components, depending upon the assay. The first bibulous member transfers the fluid to the sample pad. The second bibulous member receives the transport fluid from the sample pad and serves as a bridge to transfer the transport fluid from the sample pad to the assay measurement region. The sample is prevented from interacting with the two bibulous members when sample is transferred to the pad by a separation means, usually an inert non-porous film, which blocks transfer from the sample pad to the bibulous members. The amount of sample accepted by the sample pad and involved in the assay medium may be controlled by providing for transfer of fluid beyond the amount saturating the pad through a non-wetting screen into an absorbant layer. After addition of the sample to the sample pad, and an incubation of from 1 to 30 minutes, the porous non-wetting material and absorbant layer are removed, leaving the sample pad as the sole repository of sample for the assay.

The following examples are offered by way of illustration and not by way of limitation.

EXPERIMENTAL

The Dry Reagent Pad contains:

| REAGENT: | | |
|---|---|---|
| Cholesterol Esterase | 0.18μ | Enzymes |
| Cholesterol Oxidase | 0.50μ | |
| Sodium Cholate | 1% | Detergents |
| Nonidet PL 40 TM | 1% | |
| Mega −8 TM | 1% | |
| NaK Tartrate | 0.025M | Additives |
| Nitroprusside | 0.025M | |
| Na Stannate | 0.025M | |
| Na Azide | 0.01% | |
| Gum Arabic | 2% | Enzyme Stabilizers |
| Gelatin | 0.5% | |
| Gantrez | 0.5% | |
| Sucrose | 5% | |

TABLE 1

$H_2O_2$ STABILITY IN PROBLEMATIC[1] PATIENT SERUM WITH AND WITHOUT STABILIZERS[2]

| Patient Serum # | Hydrogen Peroxide Recovery (%) | |
|---|---|---|
| | Without Stabilizers | With Stabilizers[2] |
| Control[3] | — | 92.5 |
| Pool #1 | 6 | 89.7 |
| Sample #33 | 48 | 90.7 |
| Sample #38 | 20 | 93.6 |
| | Hydrogen Peroxide Recovery (%) | |

TABLE 1-continued $H_2O_2$ STABILITY IN PROBLEMATIC[1] PATIENT SERUM WITH AND WITHOUT STABILIZERS[2]

| Patient Serum # | Without Stabilizers | With Stabilizers[2] |
|---|---|---|
| Sample #4 | 39 | 87.3 |

PROTOCOL: 10 μl of $H_2O_2$ (3.26 to 4.63 mM) was added to 10 μl of patient serum and incubated for 20 minutes in a 12 × 75 mm test tube. One ml of a horseradish peroxidase (HRP) (25 μg/ml) and 4-cl-l-naphthol substrate solution (200 μg/ml) is added and the end point color is measured after 10 minutes. In this way $H_2O_2$ recovery is measured.
[1]Problematic serum samples gave the lowest recovered $H_2O_2$ out of 40 samples which were evaluated.
[2]Stabilizers are 25 mM Sodium Potassium Tartrate, 25 mM Sodium Stannate, 25 mm Sodium Nitroprusside, and 0.01% Sodium Azide.
[3]The control used was done by adding 10μ serum, then 10 μl of $H_2O_2$ to 1 ml of HRP-substrate solution. The best expected $H_2O_2$ recovery is 92.5%. All samples tested gave numbers very close to this value when the stabilizers were present.

TABLE 2

STRIP ASSAY MIGRATION HEIGHT STABILITY WITH STABILIZERS COIMMOBILIZED ON ENZYME REAGENT PAD

| Time (Min) | Migration Ht. (mm) |
|---|---|
| 1 | 24.5 |
| 3 | 28.0 |
| 5 | 25.0 |
| 10 | 26.0 |
| 15 | 25.0 |

PROTOCOL: 10 μl of serum sample #4 was added to each of 5 assay strips* and incubated for 1, 2, 5, 10, & 15 minutes. The migration height was measured and recorded. The data above shows that the migration height is stable for at least 15 minutes even with this problematic serum sample.
*A sample strip is prepared as follows. The support layer is composed of polystyrene rigid backing material of 0.01 inch thick. The 3M 443 double-stick tape is provided as a first 10 mm strip beginning at one end, followed by a space of 2.5 mm, a second layer of adhesive having a width of 5 mm, followed by a space of 2.5 mm. Finally, the remainder of the support is covered with 3M 415 double-stick adhesive for a width of 80 mm. A 3 mm hole is punched through the support 15 mm from the end in order to provide the sample loading port.

The measurement or quantitation area is prepared by placing a sheet of Whatman 31ET chromatography paper having a width of 70 mm and of any convenient length, so that ultimately the strips may be cut from a larger laminated sheet.

A stock solution is prepared for attachment of the dye to the measurement area. Of particular interest is the use of modified N,N-dimethylaniline, which is N-[ω-1,2-ethylenediamine butylcarboxamido],N-methylaniline. The dimethylaniline (DMA) derivative is coupled to the paper employing carbonyldiimidazole. The paper is activated by soaking the paper in 0.20M carbonyldiimidazole in methylene chloride, followed by soaking the paper in 1.5 mg/ml DMA derivative in methylene chloride.

Following the covalent attachment of the dimethylaniline analog, the paper is soaked in a 0.5 mg/ml solution of 3-methyl-2-benzothiazolinone hydrazone (MBTH), although a concentration in the range of 0.1 to 2 mg/ml is useful. Excess solution is wiped off gently by wiping the paper over one edge of a dish, followed by drying the paper in a forced air convection oven at 50° C. for about 25 minutes. The paper is firmly laminated onto the double-stick adhesive layer in the measurement area extending from one end of the support. At the opposite end, the bridging strips are affixed to the support. The first strip beginning at the end is 13 mm long and is affixed at one end along the adhesive and overlaps the sample pad by about 1 mm. The second strip is 14 mm long and overlaps the sample pad by about 1 mm. In addition, the second strip is placed over the second strip of adhesive extending from the sample pad to the measurement area, while overlapping both the measurement area and sample pad by about 1 mm.

The sample pad is conveniently of cellulose chromatography paper, but glass fiber paper, synthetic membrane, or other suitable material may be employed. Conveniently, the pad is 5 mm × 5 mm.

Once the sheet has been assembled, the sheet may now be cut into 5-mm strips, so as to provide the final device. The strip is now ready to be used in an assay.

The immobilization reagent for the enzymatic conversion pad contains one of the following formulations.

| FORMULATION FOR CONVERSION PAD | |
|---|---|
| Formulation #1: | |
| 1. 0.43M Sodium Phosphate Buffer pH 7.0 | 462 μL |
| 2. 12.5% Sucrose | 100 μL |
| 3. 10% Nonidet P-40 | 100 μL |
| 4. 10% Sodium Cholate | 100 μL |
| 5. 10% Mega-8 | 83 μL |
| 6. 1M NaK Tartrate | 25 μL |
| 7. 1M Na Nitroprusside | 25 μL |
| 8. 1M Na Stannate | 25 μL |
| 9. 2.5% Na Azide | 4 μL |
| 10. 500 u/ml Cholesterol Esterase | 36 μL |
| 11. 1250 u/ml Cholesterol Esterase | 40 μL |
| Total: | 1.0 mL |
| Formulation #2: | |
| 1. 20% Gum Arabic | 100 μL |
| 2. 5% Gelatin | 100 μL |
| 3. 5% Gantrez AN-149 | 100 μL |
| 4. 50% Sucrose | 100 μL |
| 5. 10% Nonidet P-40 | 100 μL |
| 6. 10% Sodium Cholate | 100 μL |
| 7. 10% Mega-8 | 83 μL |
| 8. 1M NaK Tartrate (Sigma) 25 mM | 25 μL |
| 9. 1M Na Nitroprusside (Sigma) | 25 μL |
| 10. 1M Na Stannate (Alfa) | 25 μL |
| 11. 2.5% Na Azide (Sigma) | 4 μL |
| 12. 500 u/mL Cholesterol Esterase | 36 μL |
| 13. 1250 u/mL Cholesterol Oxidase | 40 μL |
| 14. 1M Sodium Phosphate pH 7.0 | 162 μL |
| Total: | 1.0 mL |

It is evident from the above results, that the subject composition provides for stabilization of hydrogen peroxide, so as to allow for quantitation of the hydrogen peroxide in the presence of components of blood. In this manner, assays can be carried out either in the liquid phase or on a bibulous support, where the amount of hydrogen peroxide produced in relation to an analyte may be quantitated. The composition does not interfere with the other aspects of the assay, so as to allow for an accurate and simple method for determining a wide variety of analytes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a method for determining hydrogen peroxide in an assay in the presence of components of blood resulting in the reduction of detectable hydrogen peroxide, the improvement which comprises:

including with said hydrogen peroxide a stabilizing amount of a composition comprising stannate, nitroprusside, and an hydroxylated carboxylate chelating agent in a molar ratio of 0.2–5:0.2–5:0.2–5 in an amount to provide individual concentrations in the assay medium in the range of about 0.0001 to 0.5M, and an azide as a catalase inhibitor in from about $1 \times 10^{-4}$ to 0.1 weight percent of said composition.

2. A method according to claim 1, wherein said method comprises an assay employing an enzyme which produces hydrogen peroxide.

3. A method according to claim 2, wherein said enzyme is cholesterol oxidase, glucose oxidase, uric oxidase, alcohol oxidase or xanthine oxidase.

4. A method according to claim 1, wherein said determination is made on a bibulous strip.

5. A method according to claim 1, wherein said determination is made in solution.

6. An assay method for determining an analyte in a blood sample where hydrogen peroxide is produced in an amount in relation to the amount of analyte present in an assay medium, said method comprising:

combining said sample with reagents for producing hydrogen peroxide in an amount in relation to the amount of analyte present in said sample, and a hydrogen peroxide stabilizing amount of a composition comprising stannate, nitroprusside and tartrate in a molar ratio of 0.2–5:0.2–5:0.2–5 in an amount to provide individual concentrations in said assay medium in a range from about 0.001 to 0.1M, and azide in a range of $1 \times 10^{-4}$ to 0.1 weight percent of said composition; and determining the amount of hydrogen peroxide as indicative of the amount of analyte in said sample.

7. A method according to claim 6, wherein said analyte is cholesterol.

8. A method according to claim 6, wherein said analyte is glucose.

9. A method according to claim 6, wherein said analyte is alcohol.

10. A method according to claim 6, wherein said reagents comprise an enzyme which produces hydrogen peroxide, and said determining employs horseradish peroxidase.

11. A method according to claim 10, wherein said determining comprises detection of a chromogen.

12. A method according to claim 10, wherein said enzyme is glucose oxidase or cholesterol oxidase.

13. A method according to claim 6, wherein said stannate and tartrate are sodium and/or potassium salts.

14. A method according to claim 13, wherein said method is performed on a solid bibulous layer.

15. A method according to claim 13, wherein said method is performed in solution.

16. A composition comprising stannate, nitroprusside and tartrate in mole ratios of stannate, nitroprusside and tartrate of about 0.2–5:0.2–0.5:0.2–5.

17. A composition according to claim 16, further comprising azide.

18. A composition according to claim 17, impregnated on a bibulous support.

19. A composition according to claim 17, wherein said composition is a powder.

20. A composition according to claim 16, further comprising detergents and enzyme stabilizers.

* * * * *